United States Patent
Yokhin

(10) Patent No.: US 7,076,024 B2
(45) Date of Patent: Jul. 11, 2006

(54) X-RAY APPARATUS WITH DUAL MONOCHROMATORS

(75) Inventor: Boris Yokhin, Nazareth Illit (IL)

(73) Assignee: Jordan Valley Applied Radiation, Ltd., Migdal Ha'emek (IL)

( * ) Notice: Subject to any disclaimer, the term of this patent is extended or adjusted under 35 U.S.C. 154(b) by 0 days.

(21) Appl. No.: 11/000,053

(22) Filed: Dec. 1, 2004

(65) Prior Publication Data

US 2006/0115047 A1   Jun. 1, 2006

(51) Int. Cl.
*G01N 23/20* (2006.01)

(52) U.S. Cl. .......................................... 378/70; 378/86
(58) Field of Classification Search ................. 378/50, 378/70, 71, 84, 85, 86, 88, 89, 90
See application file for complete search history.

(56) References Cited

U.S. PATENT DOCUMENTS

| | | | |
|---|---|---|---|
| 4,725,963 A | 2/1988 | Taylor et al. .................. 702/40 |
| 4,989,226 A | 1/1991 | Woodbury et al. ........... 378/145 |
| 5,151,588 A | 9/1992 | Kiri et al. ................. 250/208.1 |
| 5,574,284 A | 11/1996 | Farr ....................... 250/370.06 |
| 5,619,548 A | 4/1997 | Koppel ........................ 378/70 |
| 5,740,226 A | 4/1998 | Komiya et al. ................ 378/70 |
| 5,923,720 A | 7/1999 | Barton et al. .................. 378/84 |
| 5,949,847 A | 9/1999 | Terada et al. .................. 378/90 |
| 5,963,329 A | 10/1999 | Conrad et al. ............... 356/613 |
| 6,023,496 A * | 2/2000 | Kuwabara ..................... 378/45 |
| 6,041,098 A | 3/2000 | Touryanski et al. ........... 378/70 |
| 6,192,103 B1 | 2/2001 | Wormington et al. ......... 378/73 |
| 6,226,347 B1 | 5/2001 | Golenhofen ................. 378/45 |
| 6,226,349 B1 | 5/2001 | Schuster et al. ............... 378/84 |
| 6,381,303 B1 | 4/2002 | Vu et al. ....................... 378/46 |
| 6,389,102 B1 | 5/2002 | Mazor et al. .................. 378/89 |
| 6,453,006 B1 | 9/2002 | Koppel et al. ................ 378/86 |
| 6,507,634 B1 | 1/2003 | Koppel et al. ................ 378/54 |
| 6,512,814 B1 | 1/2003 | Yokhin et al. ................ 378/82 |
| 6,556,652 B1 | 4/2003 | Mazor et al. .................. 378/86 |
| 6,639,968 B1 | 10/2003 | Yokhin et al. ................ 378/70 |
| 6,643,354 B1 | 11/2003 | Koppel et al. ................ 378/86 |
| 6,680,996 B1 | 1/2004 | Yokhin et al. ................ 378/70 |
| 6,711,232 B1 | 3/2004 | Janik ........................... 378/70 |
| 6,744,950 B1 | 6/2004 | Aleksoff ....................... 385/48 |

(Continued)

FOREIGN PATENT DOCUMENTS

JP   9-308339   12/1997

OTHER PUBLICATIONS

Wiener et al., "Characterization of Titanium Nitride Layers by Grazing-Emission X-Ray Fluorescence Spectrometry", in Applied Surface Science 125 (1998), pp. 129-136.

(Continued)

*Primary Examiner*—Courtney Thomas
(74) *Attorney, Agent, or Firm*—Smith, Gambrell & Russell

(57) ABSTRACT

X-ray apparatus, consisting of a single X-ray tube which is adapted to generate X-rays and a first optic which is adapted to focus a first portion of the X-rays onto a region of a sample via a first beam path, thereby generating first scattered X-rays from the region. The apparatus also includes a second optic which is adapted to focus a second portion of the X-rays onto the region of the sample via a second beam path, different from the first beam path, thereby generating second scattered X-rays from the region. A detector assembly simultaneously collects the first and the second scattered X-rays.

36 Claims, 3 Drawing Sheets

U.S. PATENT DOCUMENTS

| | | | |
|---|---|---|---|
| 6,750,952 B1 | 6/2004 | Grodnensky et al. | 355/77 |
| 6,771,735 B1 | 8/2004 | Janik et al. | 378/70 |
| 2001/0028699 A1 | 10/2001 | Iwasaki | 378/84 |
| 2001/0043668 A1 | 11/2001 | Hayashi et al. | 378/89 |
| 2002/0097837 A1 | 7/2002 | Fanton et al. | 378/82 |
| 2002/0110218 A1 | 8/2002 | Koppel et al. | 378/86 |
| 2003/0157559 A1 | 8/2003 | Omote et al. | 435/7.1 |
| 2004/0052330 A1 | 3/2004 | Koppel et al. | 378/46 |
| 2004/0156474 A1 | 8/2004 | Yokhin et al. | 378/70 |
| 2004/0218717 A1 | 11/2004 | Koppel et al. | 378/70 |

OTHER PUBLICATIONS

Hayashi et al., "Refracted X-Rays Propagating Near the Surface under Grazing Incidence Condition", Spectrochimica Acta, Part B 54, 1999, pp. 227-230.

Series 5000 Model XTF5011 X-Ray Tube Information, Oxford Instruments Inc., Scotts Valley, GA, U.S.A., Jun. 1998.

Monolithic Polycapillary Lens Information, X-Ray Optical Systems, Inc. Albany, NY, U.S.A., Dec. 29, 1998. (web site: www.xos.com).

S. Di Fonzo et al., "Non-Destructive Determination of Local Strain with 100-Nanometre Spatial Resolution", Nature, vol. 403, Feb. 10, 2000. (web site : www.nature.com).

Hugues Guerault, "Specular reflectivity and off-specular scattering", Tools for roughness investigation, Dec. 2000.

Jones, et al., "Small angle x-ray scattering for sub-100 nm pattern characterization", Applied Physics Letters 83:19 (2003), pp. 4059-4061.

Hu et al., "Small angle x-ray scattering metrology for sidewall angle and cross section of nanometer scale line gratings", Journal of Applied Physics 96:4 (2004), pp. 1983-1987.

Wu et al., "Small angle neutron scattering measurements of nanoscale lithographic features", Journal of Applied Physics 88:12 (2000), pp. 7298-7303.

Kojima, et al., "Structural characterization of thin films by x-ray reflectivity", Rigaku Journal 16:2 (1999), pp. 31-41.

Stommer, "X-ray scattering from silicon surfaces", in Semiconductor International (May 1, 1998).

Yoneda, "Anomalous surface reflection of X Rays", Physical Review 131, pp. 2010-2013, 1963.

Stommer, et al., "Characterization of semiconductor materials by X-ray scattering", Electrochemical Society Proceedings vol. 99-16, pp. 117-133, 1999.

Bowen, et al., "X-Ray metrology by diffraction and reflectivity", Characterization and Metrology for ULSI Technology, 2000 International Conference (American Institute of Physics, 2001), pp. 570-579.

Ulyanekov, "Introduction to high resolution X-Ray diffraction", Workshop on X-ray characterization of thin layers (Uckley, May 21-23, 2003).

Ito, "X-ray Scattering Method for Determining Pore-Size Distribution in Low-k Thins Films", Presented at the International Sematech Ultra-Low-k Workshop (San Francisco, CA, Jun. 6-7, 2002).

Naudon, et al., "New apparatus for grazing X-ray reflectometry in the angle-resoived dispresive mode", J. Appl. Cryst. 1989, vol. 22, pp. 460-464.

N. Wu, et al, "Substepping and its Application to HST Imaging", Jul. 28, 2003.

Wormington, Characterization of Pore Size Distribution in Low k Dielectrics Using X-ray Reflectvity, presented at the Sematech Gate Stack Engineering Workshop (Austin, Texas, May 2, 2002).

J. Spear, "Metrology for low-k materials", Silknet Aliance, 2003.

J.R. Levine Parrill, et al, "GISAXS—Glancing Incidence Small Angle X-ray Scattering", Journal de Physique IV 3 (Dec. 1993), pp. 411-417.

Jaklevic, et al., "High Rate X-Ray Fluorescence Analysis by Pulsed Excitation", IEEE Transactions on Nuclear Science NS-19:3 (1972), pp. 392-395.

Jaklevic, et al., "Small X-Ray Tubes for Energy Dispersive Analysis Using Semiconductor Spectrometers", Advances in X-Ray Analysis 15 (1972), pp. 266-275.

Jaklevic, et al., "Energy Dispersive X-Ray Fluorescence Spectrometry Using Pulsed X-Ray Excitation", Advances in X-Ray Analysis 19 (1976).

\* cited by examiner

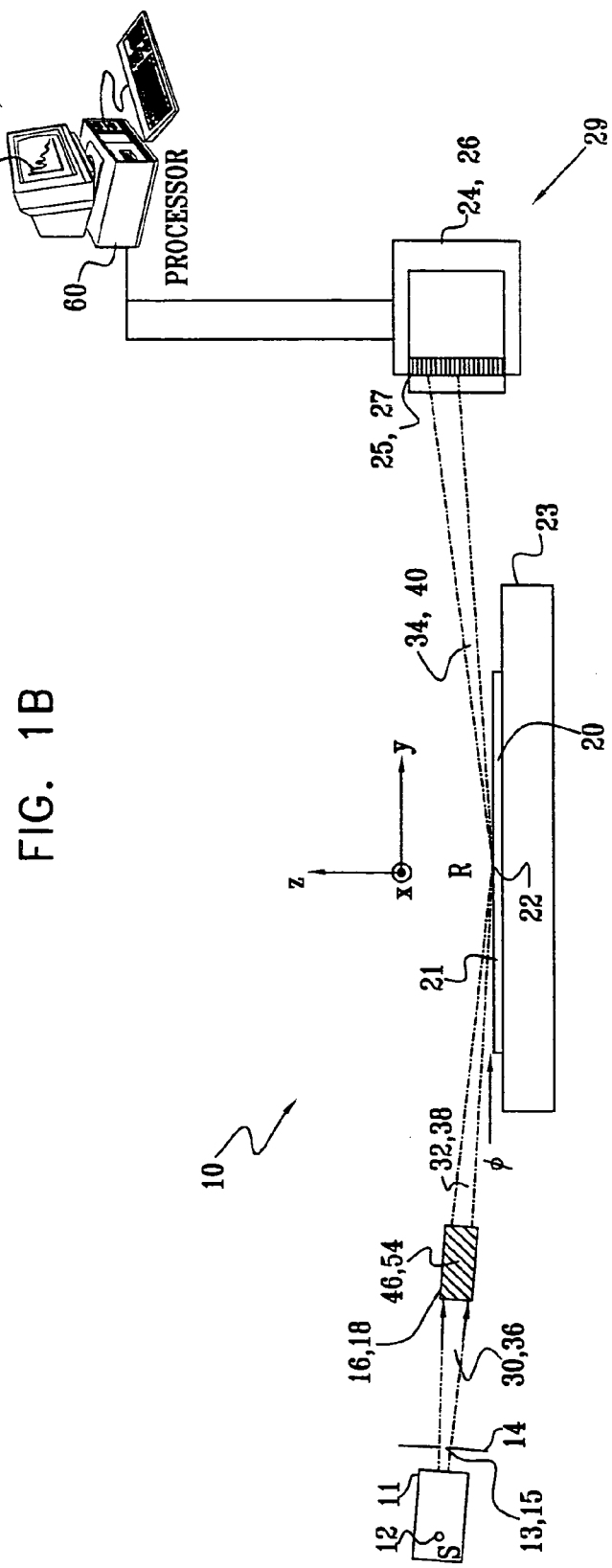

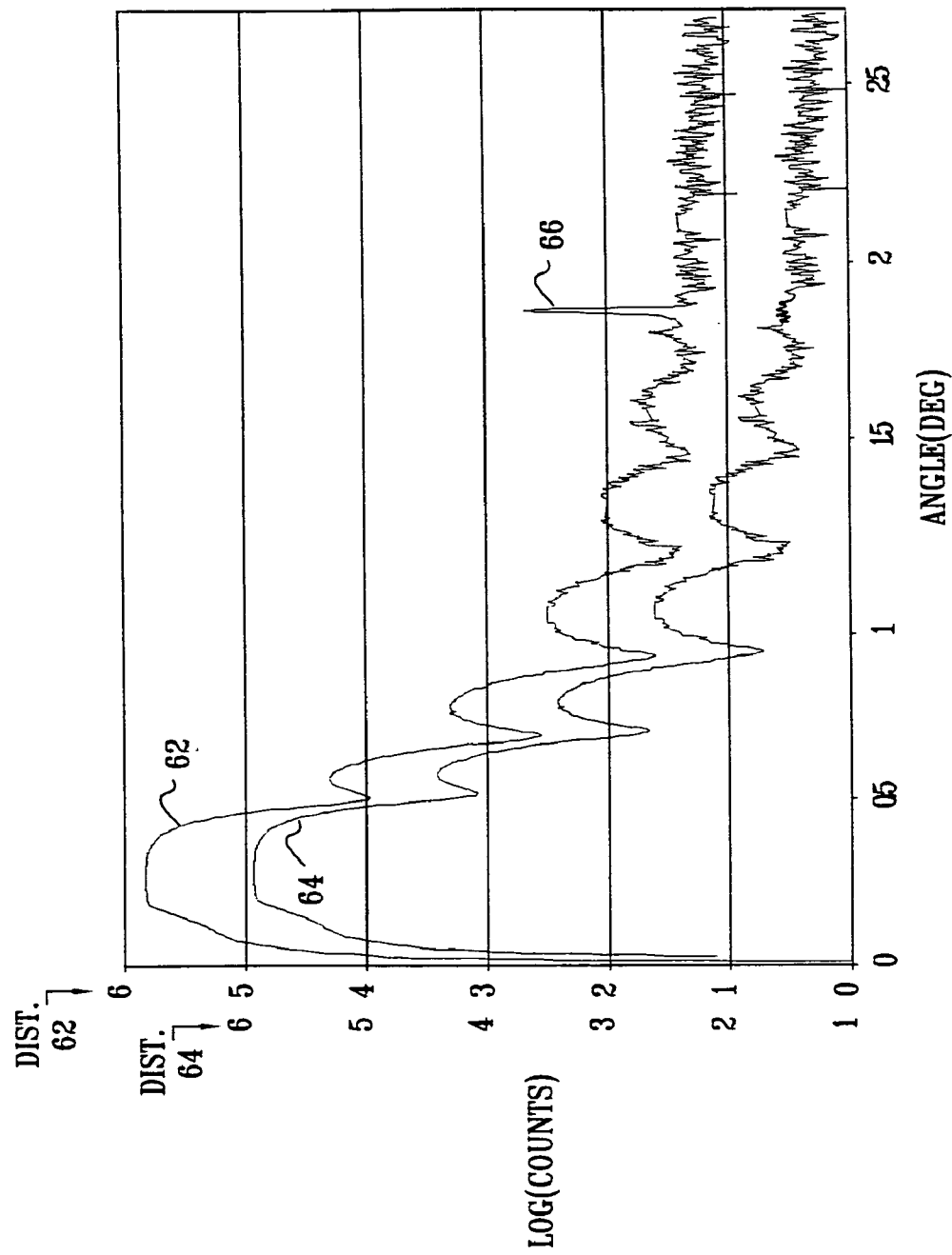

X-RAY APPARATUS WITH DUAL MONOCHROMATORS

FIELD OF THE INVENTION

The present invention relates generally to analytic instruments, and particularly to analytic instruments and methods using X-ray scattering.

BACKGROUND OF THE INVENTION

X-ray reflectometry (XRR) is a well-known technique for measuring the thickness, density and surface quality of thin film layers deposited on a substrate. Such reflectometers typically operate by irradiating a sample with a beam of X-rays at grazing incidence, i.e., at a small angle relative to the surface of the sample, in the vicinity of the total external reflection angle of the sample material. Measurement of the X-ray intensity reflected from the sample as a function of angle gives a pattern of interference fringes, which is analyzed to determine the properties of the film layers responsible for creating the fringe pattern. The X-ray intensity measurements are commonly made using a position-sensitive detector.

Various types of position-sensitive X-ray detectors are known in the art of reflectometry. Solid-state arrays typically comprise multiple detector elements, which are read out by a charge-coupled device (CCD) or other scanning mechanism. The signals at low angles, below the total external reflection angle, are usually much stronger than the signals above this angle, although in both cases there may be random, relatively large signal excursions.

In order to obtain accurate measurements of reflected beams, it is necessary to precisely calibrate the angular scale of the reflection. Such a calibration requires, inter alia, exact control of the zero angle of reflection, so that the angle of the reflected beam relative to the surface can be determined accurately. (In the context of the present patent application and in the claims, the term "zero angle" refers to the orientation of a tangent to the reflecting surface at the point of incidence of the radiation.) To make reflectometric measurements with optimal accuracy, the zero angle at the measurement point should be known to within 0.001°.

Although semiconductor wafers appear to be flat, in practice wafers typically deform slightly when held by a vacuum chuck during production or inspection. The deformation is due both to the vacuum force exerted by the chuck and to the weight of the wafer itself. Furthermore, the chuck may have imperfections, such as a slight bend in its axis, that cause deviations in the zero angle of the wafer as it rotates. As a result, inclination of the surface at different sample points on the surface of a wafer may vary by as much as 0.1–0.2°. Therefore, to perform accurate reflectometric measurements at a well-defined measurement point, it becomes necessary to recalibrate the zero angle at each point that is tested on the wafer surface.

In an X-ray reflectometer, the irradiating X-ray beam is typically filtered in a monochromator, and is also focused onto a small region of the surface being analyzed. A number of systems which act both as a monochromator and as a focusing element are known in the art. Such combined systems typically use curved crystals, the operation of which is based on the Bragg X-ray reflection law:

$$n\lambda = 2d \sin(\theta_B) \quad (1)$$

where n is a diffractive order of X-rays of wavelength $\lambda$ diffracted from crystal planes having a spacing d, and $\theta_B$ is the angle between an incident X-ray beam and the crystal planes.

U.S. Pat. No. 5,923,720, to Barton et al., whose disclosure is incorporated herein by reference, describes an X-ray spectrometer based on a curved crystal monochromator. The monochromator has the shape of a tapered logarithmic spiral, which is described as achieving a finer focal spot on a sample surface than prior art monochromators, a number of which are also described in the disclosure.

U.S. Pat. No. 6,711,232, to Janik, whose disclosure is incorporated herein by reference, describes X-ray measurements using a linear X-ray source having an axis at right angles to the surface of a sample being measured. A beam from the source is focused by a reflector onto the sample. Alternative arrangements describe two linear sources with axes at right angles to the sample surface. The two sources generate respective X-ray beams which are focused by two reflectors onto the sample.

XOS Inc., of Albany, N.Y., produce the Doubly-Bent Focusing Crystal Optic, which comprises a single crystal having two orthogonal radii of curvatures. The two radii of curvatures enable the crystal to act both as a focusing element and as a monochromator. Crystals having two radii of curvatures in different directions, such as those exemplified by the Doubly-Bent Focusing Crystal Optic, are herein termed doubly-curved crystals (DCCs) or DCC optics. DCC optics are formed from crystals such as mica, quartz, or silicon.

DCC optics typically incorporate an idea first suggested in 1882 by Rowland for optical gratings. Rowland demonstrated that a grating ruled on a spherical mirror having a radius 2R would focus all orders of spectra from the mirror onto a circle of radius R if the source of radiation irradiating the curved grating is also on the circle. The circle is termed the Rowland circle. The X-ray source, the DCC optic, and the focused image of the X-ray source all lie on the Rowland circle.

SUMMARY OF THE INVENTION

In embodiments of the present invention a plurality of focusing optics, typically two optics, focus a respective plurality of irradiating X-ray beams from different directions onto a single region, such as a region of a semiconductor wafer surface being inspected by the X-rays. Typically, the focusing optics comprise crystal monochromators, which both focus and monochromatize the X-ray beam. Each of the beams scatters from the single region, and the scattered beams are collected by a detector assembly, which may comprise a respective plurality of detectors. Focusing the plurality of beams onto the single region, and then collecting the scattered beams, enables multiple simultaneous, independent X-ray scattering measurements to be made of the single region.

The multiple independent measurements, and the increased irradiating power, substantially increase an overall signal-to-noise ratio (SNR) for the system. In addition to improving the overall SNR, using a plurality of irradiating X-ray beams following different beam paths enables random large signal excursions from one of the beams to be rejected. Furthermore, in the case of wafer inspection, the different incoming beam directions of the different paths facilitate accurate determination of the zero angle at the irradiated region.

The X-ray beams are generated from a single anode in a single X-ray tube, the single anode effectively acting as an X-ray point source. Using a single X-ray tube to produce multiple X-ray beams reduces both the cost and the size of the apparatus, compared to prior art multiple-beam systems.

In an exemplary embodiment, there are two crystal monochromators which are each formed as doubly curved crystals (DCCs), each of the crystals being curved to have substantially similar radii of curvature. The geometry of the paths of the beams reflected by the DCCs enables the latter to be arranged on a circle orthogonal to a line between the X-ray source and the single region, the circle being centered on the line. Such an arrangement may be implemented without complicated alignment.

Although the embodiments described herein are directed primarily to XRR measurements, the principles of the present invention may also be applied in other types of X-ray scattering measurements, such as X-ray diffraction (XRD), as well as other radiation-based systems for analysis and/or investigation of materials and/or thin film measurements.

There is therefore provided, according to an embodiment of the present invention, an X-ray apparatus, including:

a single X-ray tube which is adapted to generate X-rays;

a first optic which is adapted to focus a first portion of the X-rays onto a region of a sample via a first beam path, thereby generating first scattered X-rays from the region;

a second optic which is adapted to focus a second portion of the X-rays onto the region of the sample via a second beam path, different from the first beam path, thereby generating second scattered X-rays from the region; and a detector assembly which is adapted to simultaneously collect the first and second scattered X-rays.

In an embodiment, at least one of the first optic and the second optic is adapted to act as a monochromator.

In an alternative embodiment, the first and the second optics include doubly-curved crystals having identical curvatures. Typically, the first optic and the second optic are symmetrically disposed about a line joining the X-ray tube and the region.

In a disclosed embodiment, the sample defines a plane, and the sample and the first and the second beam paths are configured so that first incident beam elevation angles between the first portion of the X-rays and the plane are equal to second incident beam elevation angles between the second portion of the X-rays and the plane. The first and second incident beam elevation angles may include angles between zero and a total external reflection angle of the sample. Alternatively or additionally, the first and second incident beam elevation angles may include angles greater than a total external reflection angle of the sample.

In one embodiment, the detector assembly includes a first detector array which collects the first scattered X-rays and a second detector array which collects the second scattered X-rays. Typically, the detector assembly generates respective first and second signals responsively to the first and the second scattered X-rays, and the apparatus further includes a processor which is adapted to combine the first and second signals to output a spectrum, and to determine a property of the sample in response to the spectrum. The property may include a tilt angle of the sample.

The scattered X-rays may include reflected X-rays, and the spectrum may include an X-ray reflectance spectrum. The sample may include a thin surface layer, and the processor may be adapted to analyze the reflectance spectrum so as to determine at least one of a thickness, a density and a surface roughness of the thin surface layer.

Alternatively, the scattered X-rays include diffracted X-rays, and the spectrum includes an X-ray diffraction spectrum.

Typically, the sample includes a semiconductor wafer, and the apparatus is adapted to perform X-ray reflectometry on the semiconductor wafer, and the apparatus further includes a processor which receives an output of the detector assembly produced in response to collection of the first and second scattered X-rays therein, and which determines a property of a layer in the semiconductor wafer in response to the output.

In some embodiments, the apparatus includes one or more third optics which are adapted to focus respective one or more third portions of the X-rays onto the region of the sample via respective one or more third beam paths, thereby generating respective one or more third scattered X-rays from the region, each of the first, second, and the one or more third beam paths being different, and the detector assembly is adapted to simultaneously collect the one or more third scattered X-rays.

Typically, the single X-ray tube is operative as an approximate point source.

In another disclosed embodiment, the single X-ray tube, the first optic, and the region define a first Rowland circle, and the single X-ray tube, the second optic, and the region define a second Rowland circle, and the first and the second Rowland circles have equal radii.

In a further disclosed embodiment, the single X-ray tube, the first optic, the second optic, and the region lie in a single plane.

There is further provided, according to an embodiment of the present invention, a method for investigating a sample, including:

generating X-rays in a single X-ray tube;

directing and focusing with a first optic a first portion of the X-rays onto a region of the sample via a first beam path, thereby generating first scattered X-rays from the region;

directing and focusing with a second optic a second portion of the X-rays onto the region of the sample via a second beam path, different from the first beam path, thereby generating second scattered X-rays from the region; and simultaneously collecting the first and the second scattered X-rays.

Typically, at least one of the first optic and the second optic is adapted to act as a monochromator, and the first and the second optics include doubly-curved crystals having identical curvatures. Typically, the method includes symmetrically disposing the first optic and the second optic about a line joining the single X-ray tube and the region.

In a disclosed embodiment, the sample defines a plane, and the sample and the first and the second beam paths are configured so that first incident beam elevation angles between the first portion of the X-rays and the plane are equal to second incident beam angles between the second portion of the X-rays and the plane.

The first and second incident beam elevation angles may include angles between zero and a total external reflection angle of the sample. Alternatively or additionally, the first and second incident beam elevation angles include angles greater than a total external reflection angle of the sample.

In one embodiment, collecting the first and the second scattered X-rays includes collecting the first and the second scattered X-rays in a detector assembly including a first detector array which collects the first scattered X-rays and a second detector array which collects the second scattered X-rays. Typically, the detector assembly generates respective first and second signals from the first and the second scattered X-rays, and the method includes combining the first and second signals to output a spectrum, and determining a property of the sample in response to the spectrum. The property may include a tilt angle of the sample.

The scattered X-rays may include reflected X-rays, and the spectrum includes an X-ray reflectance spectrum.

The sample may include a thin surface layer, and the method typically includes analyzing the reflectance spectrum so as to determine at least one of a thickness, a density and a surface roughness of the thin surface layer.

Alternatively or additionally, the scattered X-rays include diffracted X-rays, and the spectrum includes an X-ray diffraction spectrum.

In a disclosed embodiment, the sample includes a semiconductor wafer. Typically, investigating the sample includes performing X-ray reflectometry on the semiconductor wafer, and the method further includes generating an output from a detector assembly in response to collecting the first and the second scattered X-rays therein, and processing the output to determine a property of a layer included in the semiconductor wafer.

In another embodiment, the method includes directing and focusing with one or more third optics respective one or more third portions of the X-rays onto the region of the sample via respective one or more third beam paths, thereby generating respective one or more third scattered X-rays from the region, and simultaneously collecting the first and the second and the one or more third scattered X-rays, and wherein each of the first, second, and the one or more third beam paths are configured to be different.

In yet another disclosed embodiment, the single X-ray tube is operative as an approximate point source.

In an alternative disclosed embodiment, the single X-ray tube, the first optic, and the region define a first Rowland circle, and the single X-ray tube, the second optic, and the region define a second Rowland circle, and the first and the second Rowland circles have equal radii.

The present invention will be more fully understood from the following detailed description of the embodiments thereof, taken together with the drawings, a brief description of which follows.

BRIEF DESCRIPTION OF THE DRAWINGS

FIG. 1A and FIG. 1B illustrate schematic top and side views of an X-ray apparatus, according to an embodiment of the present invention; and FIG. 2 shows schematic simulated plots of distributions generated by the apparatus of FIGS. 1A and 1B, according to an embodiment of the present invention.

DETAILED DESCRIPTION OF EMBODIMENTS

Figure 1A:
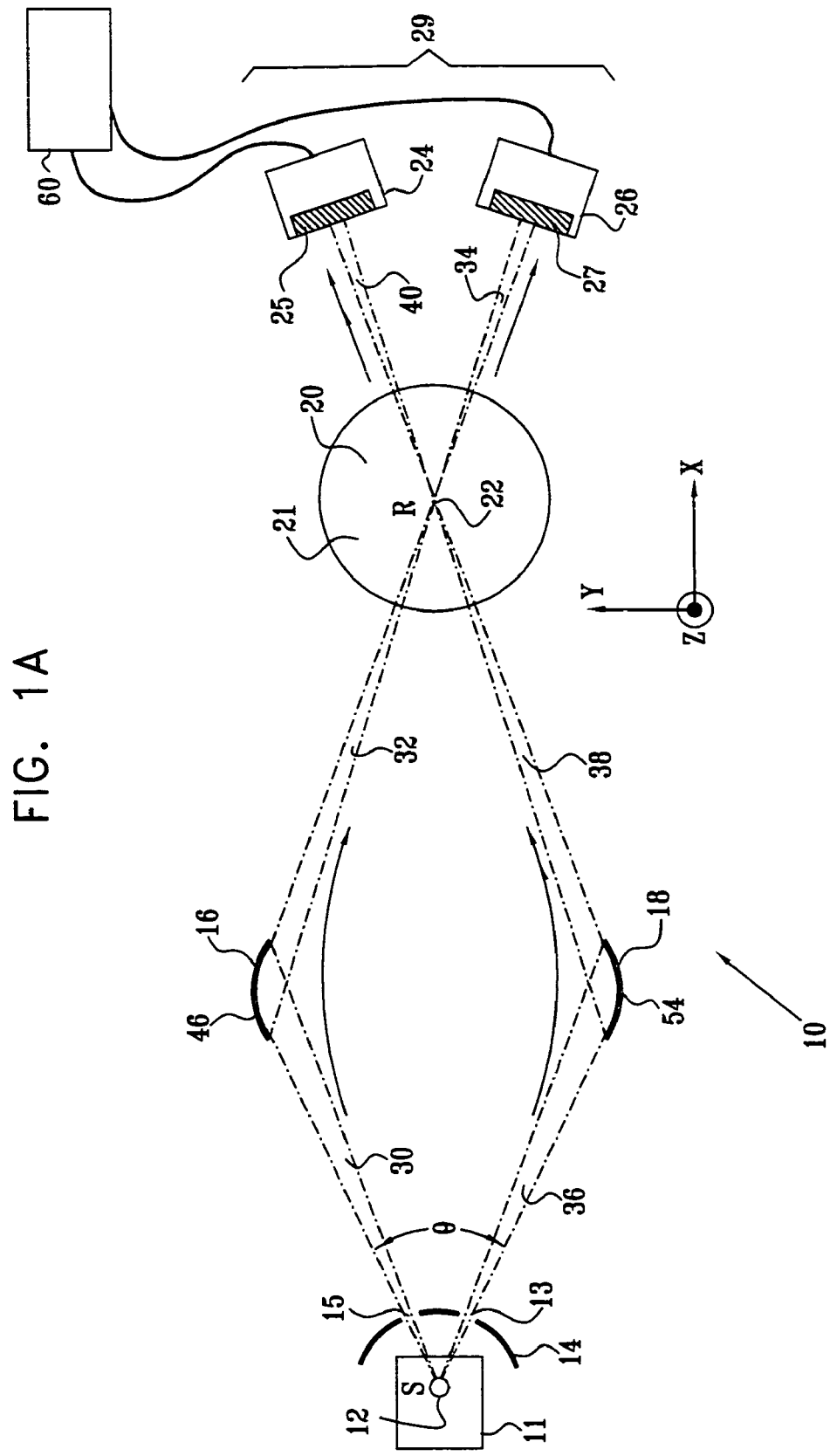

Reference is now made to FIG. 1A and FIG. 1B, which are schematic top and side views of an X-ray apparatus 10, according to an embodiment of the present invention. Like numerals in FIGS. 1A and 1B identify like elements of the apparatus. The description herein is directed, by way of example, to X-ray examination, typically comprising X-ray reflectometry (XRR) and/or diffractometry (XRD), of a region on a surface of a semiconductor wafer. The examination is typically to determine a property, such as a thickness, a density and/or a surface roughness, of a thin surface layer of the wafer. It will be understood, however, that the principles of the present invention may be applied to irradiation of substantially any type of region to which the irradiating X-rays can be directed. Such regions include the interior and/or the surface of gases, liquids and colloids, as well as the interior and/or the surface of solids.

A single X-ray tube 11, such as an XTF 5011 produced by Oxford Instruments of Scotts Valley, Calif., generates X-rays from a single anode 12. Anode 12 acts as an approximate point source S by the X-ray tube focusing its electrons onto the anode in a circle of the order of 50 microns diameter. Typically, the X-rays generated are soft X-rays, for example having energies of about 8.05 keV ($CuK\alpha_1$) or 5.4 keV ($CrK\alpha_1$). The X-rays are confined, by two apertures 13, 15 in a shield 14, into two separate beams 30 and 36 which each diverge from anode 12. Beams 30 and 36 have generally similar angles of divergence, typically approximately equal to 5°.

Diverging beam 30 irradiates a first X-ray optic 16, and beam 36 irradiates a second X-ray optic 18. Each optic acts as both a focusing element and as a monochromator. Hereinbelow, by way of example, optics 16 and 18 are assumed to comprise substantially similar doubly curved crystal (DCC) optics, and are also referred to as DCC 16 and DCC 18.

An article titled "Doubly Curved Crystals Direct X-rays" by Chen et al., published in the August 2003 edition of OE magazine, which may be found at oemagazine.com/fromTheMagazine/aug03/curvedcrystals.html, is incorporated herein by reference. The article describes how a DCC optic having two different radii of curvatures in orthogonal directions operates. A first radius of curvature of the DCC optic is set at:

$$r_H = 2R, \qquad (2)$$

where R is the radius of the Rowland circle.

The DCC optic also has a second radius of curvature, orthogonal to the first radius of curvature, having a value given by:

$$r_V = 2R \sin^2(\theta_B) \qquad (3)$$

where $\theta_B$ is the angle between an incident X-ray beam and the planes of the DCC optic, and may be found from equation (1) in the Background of the Invention.

DCCs 16 and 18 have orthogonal radii $r_H$ and $r_V$, as given by equations (2) and (3) above.

DCC 16 focuses beam 30 into a converging monochromatic beam 32 which converges to a region 22, also referred to herein as region R, on a surface 21 of a wafer 20. Wafer 20 is typically held on a mounting assembly, such as a motion stage 23, so that surface 21 is substantially horizontal, the mounting assembly allowing accurate adjustment of the position and the orientation of the wafer in all three dimensions, where an X-Y plane is defined by surface 21. Anode 12, DCC 16, and region 22 define a first plane, and they also define a first Rowland circle, of radius R, in the plane.

Incident X-rays from beam 32 scatter at region 22 to form a scattered beam 34, which is collected by a detector sub-assembly 26, comprising a detector array 27, such as a charge-coupled device (CCD). A detector assembly which may be advantageously used to perform the function of sub-assembly 26 is described in more detail in U.S. Pat. No. 6,512,814, which is incorporated herein by reference. In the specification and in the claims, the term "scatter," as well as derived terms such as "scattered" and "scattering," is assumed to comprise any sort of emission from a sample that is induced in response to an incident radiation beam, including reflection and/or diffraction of the incident radiation beam. Thus, scattered beam 34 may comprise reflection of beam 32 from region 22, and/or diffraction of beam 32 from the region.

In a similar manner to that of DCC 16, DCC 18 focuses beam 36 into a converging monochromatic beam 38 which converges to region 22. Anode 12, DCC 18, and region 22 define a second plane, and as described above for the first Rowland circle, they also define a second Rowland circle. Incident X-rays from beam 38 scatter at region 22 to form a scattered beam 40, which is collected by a detector sub-assembly 24, comprising a detector array 25. Sub-assembly 24 is typically generally similar to sub-assembly 26, and both sub-assemblies collect their beams simultaneously. In one embodiment of the present invention, the two sub-assemblies are configured as a detector assembly 29.

Since DCC 16 and DCC 18 are substantially similar in composition and construction, the wavelength of beams 32 and 38 are substantially the same. In an embodiment of the present invention, DCC 16 and DCC 18 are positioned so that beams 32 and 38 both make substantially similar elevation angles $\phi$ with surface 20 and so that the first and the second planes referred to above are substantially coincident. The elevation angle for each beam 32 and 38 may typically be in a range of 0–5° for XRR, or in a range of 30–40° for XRD. Appropriate elevation angle ranges for other types of X-ray irradiation will be apparent to those skilled in the art.

In a disclosed embodiment the positions of crystal 16 and crystal 18 are adjusted so that beams 30 and 36 make an angle $\theta$ with each other of approximately 28°, although the DCCs may be positioned to form substantially any convenient value of $\theta$. Typically, DCC 16 and DCC 18 are substantially equidistant from a line SR connecting anode 12 (S) and region 22 (R), so that the first and the second Rowland circles have substantially the same radius.

A signal processor 60 receives and analyzes the output of each detector sub-assembly 24, 26 so as to determine respective distributions 62, 64 of the flux of X-ray photons scattered from region 22 as a function of elevation angle at a given X-ray energy. By way of example, distribution 62 is illustrated schematically in FIG. 1B, and in more detail in FIG. 2. Typically, wafer 20 has one or more thin surface layers, such as thin films, at region 22. Consequently, distributions 62 and 64 exhibit a structure that is characteristic of interference and/or diffraction effects due to the surface layer and interfaces between the layers.

While the paths followed by beams 32 and 38 are different, both make similar small elevation angles with surface 20, and since the beams have similar wavelengths, distributions 62 and 64 are expected to be substantially the same. The expected similarity of the distributions may be used by processor 60 to significantly improve measurements of the distributions and derived measurements thereof, as exemplified below with reference to FIG. 2.

As noted earlier, stage 23 shifts wafer 22 in the X-Y plane to enable apparatus 10 to measure spectra at multiple locations on the surface of the wafer. The surface tilt angle of the wafer (i.e., the angle of deviation between a plane that is locally tangent to the surface and the reference X-Y plane) on stage 23 may not be perfectly uniform over the entire surface of the wafer. In a typical use of the apparatus as a reflectometer, wafer 20 is a reference wafer which is held in place on stage 23 by suction exerted through vacuum ports (not shown) in the surface of the stage. Under these circumstances, the reference wafer conforms to the shape of the stage, with deformations due to the force of the suction. As a result, the local tilt angle of the wafer may vary from point to point on the wafer surface. Accurate XRR measurement, however, requires that the tilt angle at each point be known and taken into account, so that apparatus 10 is used to generate a tilt map of the tilt angle variations over the reference wafer, and these variations are then used when wafer 20 is a production wafer.

Techniques described in U.S. patent application Ser. Nos. 10/313,280, 10/364,883, and 10/689,314, or in U.S. Pat. No. 6,680,996, which are assigned to the assignee of the present invention and which are incorporated herein by reference, may be used to generate the tilt map.

Since apparatus 10 uses simultaneous measurements of beams 32 and 38, the time required to prepare the tilt map is substantially reduced relative to prior art single-beam systems. The tilt angles, and interpolated tilt angles derived therefrom, may then be applied in order to correct the XRR results for wafer 20 as a production wafer. Typically, the angular scale of each distribution 62 and 64 of a production wafer is adjusted to account for the local tilt at the point at which the distribution was measured. Alternatively, the tilt angle of stage 23 or the positions of X-ray source S and detector sub-assemblies 24 and 26 may be adjusted to compensate for the local tilt.

FIG. 2 shows schematic simulated plots of distributions 62 and 64, according to an embodiment of the present invention. The plots show, on a logarithmic scale, the number of counts n(j) accumulated at each pixel of array 25 and array 27 as a function of reflection angle. The distributions are assumed to be generated after allowances for tilt of region 22 have been incorporated in the plots. Typically, the measurements of tilt are made as described above. For clarity, the counts scale of distribution 62 is different from that of distribution 64 so that the two distributions are clearly seen. Since both distributions 62 and 64 are determined for the same region 22 using X-rays of substantially the same wavelength, and since corrections for tilt of region 22 have been incorporated in the plots, the distributions are expected to be substantially identical.

In practice, however, random noise causes the two distributions to be different. In apparatus 10 the signal to noise ratio (SNR) is increased, compared to the SNR of single beam reflectometers or diffractometers, by averaging the two distributions in processor 60 to output a final spectrum. Furthermore, in apparatus 10, random, relatively large signal excursions, such as that exemplified by a peak 66, may be recognized and subtracted out by processor 60 before outputting the final spectrum. For example, the processor may fit distributions 62 and 64 to a curve based on the averaged distributions, and subtract out results that are greater than a predetermined number of standard deviations, such as three, from the fitted curve. After removing outliers in this fashion, the processor typically repeats the averaging and fitting process.

It will be appreciated that while the embodiments above relate to X-ray apparatus that has two separate beams, the scope of the present invention includes X-ray apparatus having three or more separate beams. As in apparatus 10, the respective focusing elements for each of the beams of such a multiple beam apparatus are typically approximately equidistant from line SR (FIG. 1A). It will also be appreciated that embodiments of the present invention may be advantageously used as part of a cluster tool, and/or in situ in a processing chamber.

It will thus be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

I claim:

1. An X-ray apparatus, comprising:
   a single X-ray tube which is adapted to generate X-rays:
   a first optic which is adapted to focus a first portion of the X-rays onto a region of a sample via a first beam path, thereby generating first scattered X-rays from the region;
   a second optic which is adapted to focus a second portion of the X-rays onto the region of the sample via a second beam path, different from the first beam path, thereby generating second scattered X-rays from the region; and
   a detector assembly which is adapted to simultaneously collect the first and second scattered X-rays, wherein the detector assembly comprises a first detector array which collects the first scattered X-rays and a second detector array which collects the second scattered X-rays.

2. The apparatus according to claim 1, where at least one of the first optic and the second optic is adapted to act as a monochromator.

3. The apparatus according to claim 1, wherein the first and the second optics comprise doubly-curved crystals having identical curvatures.

4. The apparatus according to claim 1, wherein the first optic and the second optic are symmetrically disposed about a line joining the X-ray tube and the region.

5. The apparatus according to claim 1, wherein the first detector array and the second detector array generate respective first and second signals responsively to the first and the second scattered X-rays, and comprising a processor which is adapted to combine the first and second signals to output a spectrum, and to determine a property of the sample in response to the spectrum.

6. The apparatus according to claim 5, wherein the property comprises a tilt angle of the sample.

7. The apparatus according to claim 5, wherein the first and second scattered X-rays comprise reflected X-rays, and wherein the spectrum comprises an X-ray reflectance spectrum.

8. The apparatus according to claim 7, wherein the sample comprises a thin surface layer, and wherein the processor is adapted to analyze the reflectance spectrum so as to determine at least one of a thickness, a density and a surface roughness of the thin surface layer.

9. The apparatus according to claim 5, wherein the first and second scattered X-rays comprise diffracted X-rays, and wherein the spectrum comprises an X-ray diffraction spectrum.

10. The apparatus according to claim 1, wherein the sample comprises a semiconductor wafer.

11. The apparatus according to claim 10, wherein the apparatus is adapted to perform X-ray reflectometry on the semiconductor wafer, and further comprising a processor which receives an output of detector assembly produced in response to collection of the first and second scattered X-rays therein, and which determines a property of a layer of the semiconductor wafer in response to the output.

12. The apparatus according to claim 1, and comprising one or more third optics which are adapted to focus respective one or more third portions of the X-rays onto the region of the sample via respective one or more third beam paths, thereby generating respective one or more third scattered X-rays from the region, each of the first, second, and the one or more third beam paths being different, and wherein the detector assembly is adapted to simultaneously collect the one or more third scattered X-rays.

13. The apparatus according to claim 1, wherein the single X-ray tube is operative as an approximate point source.

14. The apparatus according to claim 1, wherein the single X-ray tube, the first optic, and the region define a first Rowland circle, and wherein the single X-ray tube, the second optic, and the region define a second Rowland circle, and wherein the first and the second Rowland circles have equal radii.

15. The apparatus according to claim 1, wherein the single X-ray tube, the first optic, the second optic, and the region lie in a single plane.

16. An X-ray apparatus, comprising:
   a single X-ray tube which is adapted to generate X-rays:
   a first optic which is adapted to focus a first portion of the X-rays onto a region of a sample via a first beam path, thereby generating first scattered X-rays from the region;
   a second optic which is adapted to focus a second portion of the X-rays onto the region of the sample via a second beam path, different from the first beam path, thereby generating second scattered X-rays from the region; and
   a detector assembly which is adapted to simultaneously collect the first and second scattered X-rays, wherein the sample defines a plane, and wherein the sample and the first and the second beam paths are configured so that first incident beam elevation angles between the first portion of the X-rays and the plane are equal to second incident beam elevation angles between the second portion of the X-rays and the plane.

17. The apparatus according to claim 16, wherein the first and second incident beam elevation angles comprise angles between zero and a total external reflection angle of the sample.

18. The apparatus according to claim 16, wherein the first and second incident beam elevation angles comprise angles greater than a total external reflection angle of the sample.

19. A method for investigating a sample, comprising:
   generating X-rays in a single X-ray tube;
   directing and focusing with a first optic a first portion of the X-rays onto a region of the sample via a first beam path, thereby generating first scattered X-rays from the region;
   directing and focusing with a second optic a second portion of the X-rays onto the region of the sample via a second beam path, different from the first beam path, thereby generating second scattered X-rays from the region; and
   simultaneously collecting the first and second scattered X-rays,
   wherein collecting the first and the second scattered X-rays comprises collecting the first and the second scattered X-rays in a detector assembly comprising a first detector array which collects the first scattered X-rays and a second detector array which collects the second scattered X-rays.

20. The method according to claim 19, wherein at least one of the first optic and the second optic is adapted to act as a monochromator.

21. The method according to claim 19, wherein the first and the second optics comprise doubly-curved crystals having identical curvatures.

22. The method according to claim 19, wherein the first optic and the second optic are symmetrically disposed about a line joining the single X-ray tube and the region.

23. The method according to claim 19, wherein the detector assembly generates respective first and second signals from the first and the second scattered X-rays, and comprising combining the first and second signals to output a spectrum, and determining a property of the sample in response to the spectrum.

24. The method according to claim 23, wherein the property comprises a tilt angle of the sample.

25. The method according to claim 23, wherein the first and second scattered X-rays comprise reflected X-rays, and wherein the spectrum comprises an X-ray reflectance spectrum.

26. The method according to claim 25, wherein the sample comprises a thin surface layer, and comprising analyzing the reflectance spectrum so as to determine at least one of a thickness, a density and a surface roughness of the thin surface layer.

27. The method according to claim 23, wherein the first and second scattered X-rays comprise diffracted X-rays, and wherein the spectrum comprises an X-ray diffraction spectrum.

28. The method according to claim 19, wherein the sample comprises a semiconductor wafer.

29. The method according to claim 28, wherein investigating the sample comprises performing X-ray reflectometry on the semiconductor wafer, and comprising generating an output from a detector assembly in response to collecting the first and the second scattered X-rays therein, and processing the output to determine a property of a layer comprised in the semiconductor wafer.

30. The method according; to claim 19, and comprising directing and focusing with one or more third respective one or more third portions of the X-rays onto the region of the sample via respective one or more third beam paths, thereby generating respective one or more third scattered X-rays from the region, and simultaneously collecting the first and the second and the one or more third scattered X-rays, and wherein each of the first, second, and the one or more third beam paths are configured to be different.

31. The method according; to claim 19, wherein the single X-ray tube is operative as an approximate point source.

32. The method according; to claim 19, wherein the single X-ray tube, the first optic, and the region define a first Rowland circle, and wherein the single X-ray tube, the second optic, and the region define a second Rowland circle, and wherein the first and the second Rowland circles have equal radii.

33. The method according; to claim 19, wherein the single X-ray tube, the first optic, the second optic, and the region lie in a single plane.

34. A method for investigating a sample, comprising:
generating X-rays in a single X-ray tube;
directing and focusing with a first optic a first portion of the X-rays onto a region of the sample via a first beam path, thereby generating first scattered X-rays from the region;
directing and focusing with a second optic a second portion of the X-rays onto the region of the sample via a second beam path, different from the first beam path, thereby generating second scattered X-rays from the region; and
simultaneously collecting the first and second scattered X-rays,
wherein the sample defines a plane, and wherein the sample and the first and the second beam paths are configured so that first incident beam elevation angles between the first portion of the X-rays and the plane are equal to second incident beam elevation angles between the second portion of the X-rays and the plane.

35. The method according to claim 34, wherein the first and second incident beam elevation angles comprise angles between zero and a total external reflection angle of the sample.

36. The method according to claim 34, wherein the first and second incident beam elevation angles comprise angles greater than a total external reflection angle of the sample.

* * * * *